United States Patent
Lohith et al.

(10) Patent No.: US 10,947,382 B2
(45) Date of Patent: Mar. 16, 2021

(54) PHENYLENE ETHER COPOLYMER AND COMPOSITIONS COMPRISING SAME

(71) Applicant: SABIC Global Technologies B.V., Bergen op Zoom (NL)

(72) Inventors: Kenchaiah Lohith, Bangalore (IN); Gurunath Pozhal Vengu, Bangalore (IN); Shadaksharaswamy Puttamadappa, Bangalore (IN); Gaurav Mediratta, Bangalore (IN)

(73) Assignee: SHPP GLOBAL TECHNOLOGIES B.V., Bergen Op Zoom (NL)

( * ) Notice: Subject to any disclaimer, the term of this patent is extended or adjusted under 35 U.S.C. 154(b) by 154 days.

(21) Appl. No.: 16/337,099

(22) PCT Filed: Sep. 13, 2017

(86) PCT No.: PCT/IB2017/055534
§ 371 (c)(1),
(2) Date: Mar. 27, 2019

(87) PCT Pub. No.: WO2018/060803
PCT Pub. Date: Apr. 5, 2018

(65) Prior Publication Data
US 2020/0032054 A1 Jan. 30, 2020

Related U.S. Application Data

(60) Provisional application No. 62/400,668, filed on Sep. 28, 2016.

(51) Int. Cl.
*C08L 71/12* (2006.01)
*C08L 63/00* (2006.01)
(Continued)

(52) U.S. Cl.
CPC ............ *C08L 71/123* (2013.01); *C08G 65/38* (2013.01); *C08G 65/40* (2013.01); *C08G 65/42* (2013.01);
(Continued)

(58) Field of Classification Search
CPC ........ C08L 71/123; C08L 71/10; C08L 63/00; C08L 2205/025; C08L 2205/102;
(Continued)

(56) References Cited

U.S. PATENT DOCUMENTS 3,379,572 A * 4/1968 Gay .................... H01M 8/0267
                                                        429/414
3,970,640 A    7/1976 Yonemitsu et al.
(Continued)

FOREIGN PATENT DOCUMENTS

CN      1217994 A    6/1999
CN      1694923 A   11/2005
(Continued)

OTHER PUBLICATIONS

Y. Wu et al., "Synthesis and Characterizatien of α,ω-bis(2,6-dimethylphenol)-poly(2,6-dimethyl-4,4-phenylene oxide) Oligomers in Water and the End-Group Modification", Industrial and Engineering Chemistry Research. 2013, vol. 52, pp. 17351-47539.
(Continued)

*Primary Examiner* — Jane L Stanley
(74) *Attorney, Agent, or Firm* — Cantor Colburn LLP (57) ABSTRACT

A copolymer having the structure (I) wherein $Q^1$, $Q^2$, $Q^3$, $Q^4$, m, and n are defined herein. The copolymer can be formed by oxidative copolymerization of 2,4,6-trimethylresorcinol with a monohydric phenol. Also describes are a composition comprising the copolymer and a solvent, and a composition comprising the copolymer and a thermosetting resin.
(Continued)

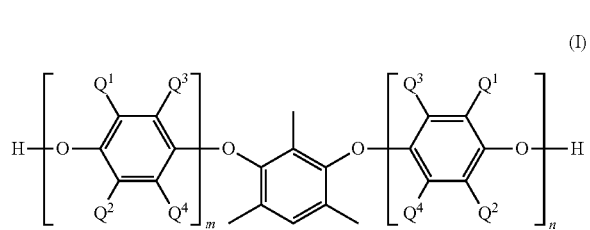

(I)

14 Claims, 6 Drawing Sheets (51) Int. Cl.
| | | |
|---|---|---|
| C08G 65/38 | (2006.01) | |
| C08G 65/42 | (2006.01) | |
| C08G 65/40 | (2006.01) | |
| B29K 71/00 | (2006.01) | |
| C07C 37/16 | (2006.01) | |

(52) U.S. Cl.
 CPC .......... *C08L 63/00* (2013.01); *B29K 2071/12* (2013.01); *C07C 37/16* (2013.01); *C08L 2205/025* (2013.01)

(58) Field of Classification Search
 CPC ........ C07C 37/16; C08G 65/40; C08G 65/38; C08G 65/42; B29K 2071/12
 See application file for complete search history.

(56) References Cited

U.S. PATENT DOCUMENTS

| | | | |
|---|---|---|---|
| 4,376,854 A * | 3/1983 | Yamaguchi | C08G 8/24 428/480 |
| 4,663,402 A | 5/1987 | Percec et al. | |
| 4,912,172 A | 3/1990 | Hallgren et al. | |
| 6,835,786 B2 | 12/2004 | Ishii et al. | |
| 7,074,861 B2 * | 7/2006 | Durairaj | C08G 8/22 525/137 |
| 7,495,047 B2 | 2/2009 | Peters et al. | |
| 7,541,421 B2 | 6/2009 | Carrillo et al. | |
| 7,582,691 B2 | 9/2009 | Peters et al. | |
| 8,053,077 B2 | 11/2011 | Braidwood et al. | |
| 8,598,281 B2 | 12/2013 | Peters | |
| 2008/0076885 A1 | 3/2008 | Yeager et al. | |
| 2009/0247032 A1 | 10/2009 | Mori et al. | |
| 2015/0166788 A1 | 6/2015 | Li et al. | |
| 2019/0336421 A1 * | 11/2019 | Maruyama | A61K 8/4966 |
| 2019/0338072 A1 * | 11/2019 | Kenchaiah | C08G 65/48 |

FOREIGN PATENT DOCUMENTS

| | | |
|---|---|---|
| CN | 102226479 A | 10/2011 |
| EP | 0436136 A1 | 5/1990 |
| GB | 550925 A | 2/1943 |
| JP | 2000143891 A | 5/2000 |
| WO | 2004072178 | 8/2004 |
| WO | 2008036454 A1 | 3/2008 |
| WO | 2008054393 A1 | 5/2008 |

OTHER PUBLICATIONS

International Search Report for International Application No. PCT/IB2017/055534; International Filing Date: Sep. 13, 2017; dated Dec. 2017; 6 pages.
Nava, Hildeberto et al., "Functional Polymers and Sequential Copolymers by Phase Transfer Catalysis", Journal of Polymer Science: Part A: Polymer Chemistry, vol. 24, 965-990 (1986).
Written Opinion of the International Search Authority for International Application No. PCT/IB2017/055534; International Filing Date: Sep. 13, 2017; dated Dec. 2017; 5 pages.

* cited by examiner

PHENYLENE ETHER COPOLYMER AND COMPOSITIONS COMPRISING SAME

CROSS-REFERENCE TO RELATED APPLICATIONS

This Application is a U.S. National Stage Application of PCT/IB2017/055534, filed Sep. 13, 2017, which claims priority to U.S. Provisional Patent Application No. 62/400,668, filed Sep. 28, 2016 both of which are incorporated by reference in their entireties herein.

BACKGROUND OF THE INVENTION

Poly(phenylene ether) polymers and oligomers have been used as additives to thermoset resins to increase toughness, decrease dielectric constant, and decrease water absorption. Initial work utilized relatively high molecular weight poly (phenylene ether) polymers having, on average, slightly less than one hydroxyl group per molecule. See, e.g., U.S. Pat. No. 4,912,172 to Hallgren et al., issued 27 Mar. 1990. Because of challenges dissolving these poly(phenylene ether)s in thermosetting resin and a desire for greater thermoset toughness for a given amount of poly(phenylene ether) additive, a preference gradually evolved for poly (phenylene ether)s that were lower in molecular weight (e.g., oligomers rather than polymers) and higher in hydroxyl functionality (e.g., molecules with about two hydroxyl groups per molecule, based on their incorporation of a dihydric phenol). For example, hydroxyl-diterminated poly (phenylene ether) oligomers have been prepared by the copolymerization of 2,6-xylenol and 2,2-bis(3,5-dimethyl-4-hydroxyphenyl)propane (also known as tetramethyl bisphenol A, or TMBPA). See, e.g., U.S. Pat. No. 8,053,077 to Braidwood et al., issued 8 Nov. 2011. Notwithstanding the success of these hydroxyl-diterminated poly(phenylene ether) oligomers as thermoset additives, there remains a desire for poly(phenylene ether) polymers and oligomers that more efficiently incorporate dihydric phenol.

BRIEF SUMMARY OF EMBODIMENTS OF THE INVENTION

One embodiment is a copolymer having the structure wherein each occurrence of $Q^1$ and $Q^2$ is independently selected from the group consisting of halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, and $C_2$-$C_{12}$ halohydrocarbyloxy wherein at least two carbon atoms separate the halogen and oxygen atoms; each occurrence of $Q^3$ and $Q^4$ is independently selected from the group consisting of hydrogen, halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, and $C_2$-$C_{12}$ halohydrocarbyloxy wherein at least two carbon atoms separate the halogen and oxygen atoms; and m and n are independently 0 to 50, provided that the sum of m and n is at least 3.

Another embodiment is a composition comprising: the copolymer in any of its variations, and a solvent selected from the group consisting of $C_3$-$C_8$ ketones, $C_3$-$C_8$ N,N-dialkylamides, $C_4$-$C_{16}$ dialkyl ethers, $C_6$-$C_{12}$ aromatic hydrocarbons, $C_1$-$C_3$ chlorinated hydrocarbons, $C_3$-$C_6$ alkyl alkanoates, $C_2$-$C_6$ alkyl cyanides, $C_2$-$C_6$ dialkyl sulfoxides, and mixtures thereof.

Another embodiment is a composition comprising: the copolymer in any of its variations, and a thermosetting resin.

These and other embodiments are described in detail below.

DETAILED DESCRIPTION OF THE INVENTION

The present inventors have determined that poly(phenylene ether) polymers and oligomers synthesized by copolymerizing 2,4,6-trimethylresorcinol with a monohydric phenol exhibit efficient incorporation of the 2,4,6-trimethylresorcinol relative to polymers and oligomers prepared by copolymerizing 2,2-bis(3,5-dimethyl-4-hydroxyphenyl)propane with a monohydric phenol.

One embodiment is a copolymer having the structure wherein each occurrence of $Q^1$ and $Q^2$ is independently selected from the group consisting of halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, and $C_2$-$C_{12}$ halohydrocarbyloxy wherein at least two carbon atoms separate the halogen and oxygen atoms; each occurrence of $Q^3$ and $Q^4$ is independently selected from the group consisting of hydrogen, halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, and $C_2$-$C_{12}$ halohydrocarbyloxy wherein at least two carbon atoms separate the halogen and oxygen atoms; and m and n are independently 0 to 50, provided that the sum of m and n is at least 3.

As used herein, the term "copolymer" refers to a molecule comprising at least three repeat units of at least two different types. The term "copolymer" therefore includes molecules commonly referred to as "co-oligomers".

In the copolymer structure, each occurrence of $Q^1$ and $Q^2$ is independently selected from the group consisting of halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, and $C_2$-$C_{12}$ halohydrocarbyloxy wherein at least two carbon atoms separate the halogen and oxygen atoms. As used herein, the term "hydrocarbyl", whether used by itself, or as a prefix, suffix, or fragment of another term, refers to a residue that contains only carbon and hydrogen unless it is specifically identified as "substituted hydrocarbyl". The hydrocarbyl residue can be aliphatic or aromatic, straight-chain, cyclic, bicyclic, branched, saturated, or unsaturated. It can also contain combinations of aliphatic, aromatic, straight chain, cyclic, bicyclic, branched, saturated, and unsaturated hydrocarbon moieties. When the hydrocarbyl residue is described as substituted, it can contain heteroatoms in addition to carbon and hydrogen. In some embodiments, each occurrence of $Q^1$ and $Q^2$ is independently hydrogen, methyl, N,N-diethylaminomethyl, N-ethylaminomethyl, and phenyl, provided that at least one of $Q^1$ and $Q^2$ is not hydrogen; each occurrence of $Q^3$ is hydrogen; and each occurrence of $Q^4$ is hydrogen, methyl, or phenyl. In some embodiments, each occurrence of $Q^1$ and $Q^2$ is independently methyl or N,N-diethylaminomethyl or N-ethylaminomethyl; and each occurrence of $Q^3$ and $Q^4$ is hydrogen.

In the copolymer structure, m and n are independently 0 to 50, or 0 to 30, or 0 to 20, or 0 to 15, or 0 to 10. The sum of m and n is at least 3, or at least 4, or at least 5. In some embodiments, the sum of m and n is 3 to 15, or 3 to 12.

In the copolymer structure, the 2,4,6-trimethylresorcinol residue can be either internal or terminal with respect to the copolymer chain. When the copolymer comprises internal 2,4,6-trimethylresorcinol residues, then m and n are each, on average, greater than zero.

In a very specific embodiment of the copolymer, the sum of m and n is 3 to 15; each occurrence of $Q^1$ and $Q^2$ is methyl or N,N-diethylaminomethyl or N-ethylaminomethyl; and each occurrence of $Q^3$ and $Q^4$ is hydrogen.

One embodiment is a composition comprising a solvent and the copolymer in any of its variations. The composition can be used as a convenient means of adding the copolymer to a thermosetting composition. Thus, one embodiment is a composition comprising: the copolymer in any of its variations; and a solvent selected from the group consisting of $C_3$-$C_8$ ketones (including acetone and methyl ethyl ketone), $C_3$-$C_8$ N,N-dialkylamides (including N,N-dimethylformamide, N-alkyl-2-pyrrolidones, such as N-methyl-2-pyrrolidone), $C_4$-$C_{16}$ dialkyl ethers (including tetrahydrofuran), $C_6$-$C_{12}$ aromatic hydrocarbons (including toluene and xylenes), $C_1$-$C_3$ chlorinated hydrocarbons (including dichloromethane and chloroform), $C_3$-$C_6$ alkyl alkanoates (including methyl acetate and ethyl acetate), $C_2$-$C_6$ alkyl cyanides (including acetonitrile), $C_2$-$C_6$ dialkyl sulfoxides (including dimethyl sulfoxides), and mixtures thereof. In some embodiments, the composition is homogeneous.

In a specific embodiment of the composition, it comprises, based on the total weight of the composition, 10 to 50 weight percent of the copolymer, and 50 to 90 weight percent of the solvent. Within these limits, the copolymer amount can be 20 to 40 weight percent, and the solvent amount can be 60 to 80 weight percent.

In another specific embodiment of the composition, it comprises based on the total weight of the composition, 10 to 50 weight percent of the copolymer; and 50 to 90 weight percent of the solvent, wherein the solvent is selected from the group consisting of N-methyl-2-pyrrolidone, methyl ethyl ketone, and combinations thereof.

Another embodiment is a thermosetting composition comprising: the copolymer in any of its variations, and a thermosetting resin.

Illustrative thermosetting resins include epoxy resins, unsaturated polyester resins, polyimide resins, bismaleimide resins, bismaleimide triazine resins, cyanate ester resins, vinyl resins, benzoxazine resins, benzocyclobutene resins, acrylics, alkyds, phenol-formaldehyde resins, novolac resins, resole resins, melamine-formaldehyde resins, urea-formaldehyde resins, unsaturated polyesters, unsaturated polyesterimides, and combinations thereof. In some embodiments, the thermosetting resin comprises an epoxy resin.

In a very specific embodiment of the thermosetting composition, it comprises, based on the total weight of the composition, 5 to 80 weight percent of the copolymer; and 20 to 95 weight percent of the thermosetting resin.

In another very specific embodiment of the thermosetting composition, representative of a copolymer masterbatch, it comprises, based on the total weight of the composition, 20 to 80 weight percent of the copolymer; and 20 to 80 weight percent of an epoxy resin.

The invention includes at least the following embodiments.

Embodiment 1

A copolymer having the structure wherein each occurrence of $Q^1$ and $Q^2$ is independently selected from the group consisting of halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, and $C_2$-$C_{12}$ halohydrocarbyloxy wherein at least two carbon atoms separate the halogen and oxygen atoms; each occurrence of $Q^3$ and $Q^4$ is independently selected from the group consisting of hydrogen, halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, and $C_2$-$C_{12}$ halohydrocarbyloxy wherein at least two carbon atoms separate the halogen and oxygen atoms; and m and n are independently 0 to 50, provided that the sum of m and n is at least 3.

Embodiment 2

The copolymer of embodiment 1, wherein the sum of m and n is 3 to 15.

Embodiment 3

The polymer of embodiment 1 or 2, wherein each occurrence of $Q^1$ and $Q^2$ is independently hydrogen, methyl, N,N-diethylaminomethyl, N-ethylaminomethyl, and phenyl, provided that at least one of $Q^1$ and $Q^2$ is not hydrogen; each occurrence of $Q^3$ is hydrogen; and each occurrence of $Q^4$ is hydrogen, methyl, or phenyl.

Embodiment 4

The copolymer of embodiment 1 or 2, wherein each occurrence of $Q^1$ and $Q^2$ is independently methyl or N,N-diethylaminomethyl or N-ethylaminomethyl; and each occurrence of $Q^3$ and $Q^4$ is hydrogen.

Embodiment 5

The copolymer of embodiment 1, wherein m and n are each, on average, greater than zero.

Embodiment 6

The copolymer of embodiment 1, wherein the sum of m and n is 3 to 15; each occurrence of $Q^1$ and $Q^2$ is methyl or N,N-diethylaminomethyl or N-ethylaminomethyl; and each occurrence of $Q^3$ and $Q^4$ is hydrogen.

Embodiment 7

A composition comprising: the copolymer of any one of embodiments 1-6; and a solvent selected from the group consisting of $C_3$-$C_8$ ketones, $C_3$-$C_8$ N,N-dialkylamides, $C_4$-$C_{16}$ dialkyl ethers, $C_6$-$C_{12}$ aromatic hydrocarbons, $C_1$-$C_3$ chlorinated hydrocarbons, $C_3$-$C_6$ alkyl alkanoates, $C_2$-$C_6$ alkyl cyanides, $C_2$-$C_6$ dialkyl sulfoxides, and mixtures thereof.

Embodiment 8

The composition of embodiment 7 comprising, based on the total weight of the composition, 10 to 50 weight percent of the copolymer; and 50 to 90 weight percent of the solvent.

Embodiment 9

The composition of embodiment 7 comprising, based on the total weight of the composition, 10 to 50 weight percent of the copolymer; and 50 to 90 weight percent of the solvent, wherein the solvent is selected from the group consisting of N-methyl-2-pyrrolidone, methyl ethyl ketone, and combinations thereof.

Embodiment 10

A composition comprising: the copolymer of any one of embodiments 1-6; and a thermosetting resin.

Embodiment 11

The composition of embodiment 10, wherein the thermosetting resin is selected from the group consisting of epoxy resins, unsaturated polyester resins, polyimide resins, bismaleimide resins, bismaleimide triazine resins, cyanate ester resins, vinyl resins, benzoxazine resins, benzocyclobutene resins, acrylics, alkyds, phenol-formaldehyde resins, novolac resins, resole resins, melamine-formaldehyde resins, urea-formaldehyde resins, unsaturated polyesters, unsaturated polyesterimides, and combinations thereof.

Embodiment 12

The composition of embodiment 10, wherein the thermosetting resin comprises an epoxy resin.

Embodiment 13

The composition of any one of embodiments 10-12 comprising, based on the total weight of the composition, 5 to 80 weight percent of the copolymer of any one of embodiments 1-6; and 20 to 95 weight percent of the thermosetting resin.

Embodiment 14

The composition of embodiment 10 comprising, based on the total weight of the composition, 20 to 80 weight percent of the copolymer of embodiment 6; and 20 to 80 weight percent of an epoxy resin.

The invention is further illustrated by the following non-limiting examples.

Preparative Example 1

This example describes the preparation of 2,4,6-trimethylresorcinol, using the components summarized in Table 1.

TABLE 1

| Component | Description |
| --- | --- |
| Methanol | Methanol, CAS Reg. No. 67-56-1, having a purity of at least 99.8 percent; obtained from Sigma-Aldrich. |
| Resorcinol | Resorcinol, CAS Reg. No. 108-46-3, having a purity at least 99.0 percent. |
| Water | Water, CAS Reg. No. 7732-18-5, having a purity of at least 99.9%, was obtained as deionized water. |
| MgO | Magnesium oxide, CAS Reg. No. 1309-48-4, having a purity of at least 93%, was obtained from Dead Sea Periclase Ltd. |
| PEG | Polyethylene glycol, CAS Reg. No. 25322-68-3, having a nominal purity of 100% and a number average molecular weight of 400 grams/mole, was obtained from Spectrum Fine Chemicals. |
| HPMAS | (Highly Purified Magnesium Aluminosilicate) Hydrous magnesium aluminosilicate, CAS Reg. No. 12174-11-7, having a purity of about 93 to 95 weight percent, obtained as ACTI-GEL ™ 208 from ActiveMinerals International LLC. |
| $Cu(NO_3)_2 \cdot 3H_2O$ | Copper (II) nitrate trihydrate, CAS Reg. No. 10031-43-3, having a purity of at least 99.5%, was obtained from Strem Chemicals. |
| Graphite | Graphite, CAS Reg. No. 7782-42-5, nominally 100% pure, was obtained as graphite from Asbury Carbon. |

A catalyst precursor was prepared using the formulation summarized in Table 2, where component amounts are expressed in parts by weight. To 85.5 grams of magnesium oxide, 4.3 grams of PEG, 4.3 grams of HPMAS, 0.9 grams of $Cu(NO_3)_2 \cdot 3H_2O$ and 0.9 gram of graphite were added and thoroughly mixed. To the resulting powder mix, 4.3 grams of water was added dropwise and dispersed by mixing. The powder mixture was pressed into 4.76 millimeters (3/16 inch) diameter pellets using a die press. The pellets were used as the catalyst precursor.

TABLE 2

| Component | Amount (pbw) |
|---|---|
| MgO | 85.5 |
| PEG | 4.3 |
| HPMAS | 4.3 |
| Water | 4.3 |
| $Cu(NO_3)_2 \cdot 3H_2O$ | 0.9 |
| Graphite | 0.9 |
| MgSt | 0.0 |

The vapor phase methylation reaction between resorcinol and methanol was conducted in a continuous packed bed reactor. The reactor is a stainless steel tube having a 12.7 millimeter (0.5 inch) inner diameter. The reactor is heated using an electric furnace.

Five (5) grams of the catalyst precursor was packed at the center of the reactor tube. Further, the catalyst bed was supported with glass beads. The catalyst precursor was calcined at 390° C. for 22 hours under nitrogen at a weight hourly space velocity (WHSV) of 0.11 hour$^{-1}$ with no back-pressure in the system. After 22 hours of calcination, the reactor temperature was raised at a rate of 0.5° C./minute to 460° C. Before the reactant feed was pumped to the reactor, the reactor pressure was increased to 270 kilopascals absolute pressure (1.7 bar gauge), and that pressure was maintained throughout the reaction time. The feed to the reactor was a homogenous solution of resorcinol and methanol (1:8 molar ratio) and water (20% of total weight). The liquid feed was pumped into the reactor using a high performance liquid chromatography (HPLC) pump at a flow rate of 0.2 millimeters/minute. As the reactor temperature was very high (350-450° C.), the liquid feed that enters into the reactor vaporizes before it encounters the catalyst. The alkylation reactions occurred in the catalyst bed, and all the gaseous material exiting the reactor passed through a condenser to form a mixture of liquid products and non-condensable gases. This mixture of liquid products and non-condensable gases was separated in a gas-liquid separator. Analysis of the unpurified reaction mixture indicated 65% conversion of resorcinol with a 62% selectivity for TMR.

To purify the TMR in the reaction mixture (mixture of liquid products), one weight part of the liquid products was washed with 2 weight parts water. This procedure was repeated two more times and removed most of the unreacted resorcinol and methanol. The product was concentrated further to produce a viscous liquid to which ten volume parts hexane were added to produce a precipitate, and the resulting liquid/solid mixture was stirred for 30 minutes at 50° C. The powder was filtered and washed 2 times with hexane to yield a crude product with 2,4,6-trimethylresorcinol of 85 weight percent purity, the primary contaminants being dimethyl resorcinols and monomethyl resorcinols. The product was further purified by crystallization as follows.

Ten (10) grams of the crude product having 85% purity was dissolved in a minimum amount of acetone (5 to 10 milliliters), and water was added slowly until turbidity was observed. The resulting mixture was stirred, then heated to dissolve the turbid particles. The mixture was filtered, and the filtrate was aside for two to three hours, during which time crystals formed. The crystals were filtered, washed with 20 milliliters of water, and dried at room temperature. The final product, 2,4,6-trimethylresorcinol, was characterized by gas chromatography, gas chromatography-mass spectrometry, and proton nuclear magnetic resonance spectroscopy. The product had a purity of 99.3 weight percent.

Example 1

This example describes the copolymerization of 2,4,6-trimethyl resorcinol (TMR) and 2,6-xylenol. Components used in the copolymerization are summarized in Table 3.

TABLE 3

| Component | Description |
|---|---|
| Toluene | Toluene, CAS Reg. No. 108-88-3, having a purity of at least 99.8 percent, was obtained from Sigma-Aldrich. |
| 2,6-Xylenol | 2,6-Xylenol, CAS Reg. No. 576-26-1, having a purity of at least 99 percent, was obtained from Sigma-Aldrich. |
| TMR | 2,4,6-Trimethylresorcinol, CAS Reg. No. 608-98-0, having a purity of 99.3 percent, prepared as described in Preparative Example 1. |
| $CU_2O$ | Cuprous oxide, CAS Reg. No. 1317-39-1, having a purity of at least 97 percent, was obtained from Sigma-Aldrich |
| HBr | Hydrobromic acid, CAS Reg. No. 10035-10-6, was obtained as a 48% aqueous solution from S D Fine-Chem Limited. |
| DBEDA | N,N'-di-tert-butylethylenediamine, CAS Reg. No. 4062-60-6, having a purity of at least 98 percent, was obtained from Sigma-Aldrich. |
| DBA | Di-n-butylamine, CAS Reg. No. 111-92-2, having a purity of at least 98 percent was obtained from Sigma-Aldrich. |
| DMBA | N,N-Dimethylbutylamine, CAS Reg. No. 927-62-8, having a purity of at least 98 percent, obtained from Sigma-Aldrich. |
| DADMAC | N,N,N'N'-Didecyldimethyl ammonium chloride, CAS Reg. No. 7173-51-5, having a purity of at least 98 percent, obtained from Sigma-Aldrich. |
| $Na_3NTA$ | Nitrilotriacetic acid trisodium salt, CAS Reg. No. 5064-31-3, having a purity of at least 98 percent, obtained from Sigma-Aldrich |

To an oxidative coupling reactor equipped with overhead stirrer, air inlet tube, and thermometer was added a reactant mixture comprising toluene (100 milliliters), 2,6-xylenol (9 grams, 73.7 millimoles), 2,4,6-trimethylresorcinol (2 grams, 13.1 millimoles), and a catalyst solution comprising cuprous oxide (16 milligrams, 0.224 millimoles Cu), di-N-butylamine (180 milligrams, 1.39 millimoles), N,N-dimethyl-N-butylamine (580 milligrams, 5.72 millimoles), N,N'-di-tert-butylethylenediamine (30 milligrams, 0.174 millimoles), and hydrobromic acid (92 milligrams of a 48 weight percent aqueous solution, corresponding to 0.455 millimoles bromide ion). The catalyst solution was pre-mixed by dissolving the cuprous oxide, hydrobromic acid solution, and the amines in 10 milliliters toluene.

Air (as an oxygen source) was added in to the vigorously stirred solution. The temperature was maintained at 45° C. during the reaction. The reaction was continued for two hours, over which time the solution became viscous. To terminate the reaction, the air flow was cut off and an aqueous solution of trisodium nitrilotriacetate was added to the reaction mixture. The organic and aqueous layers were separated, and toluene was removed from the organic layer. The solid residue was analyzed by nuclear magnetic resonance spectroscopy (NMR).

Figure 1:
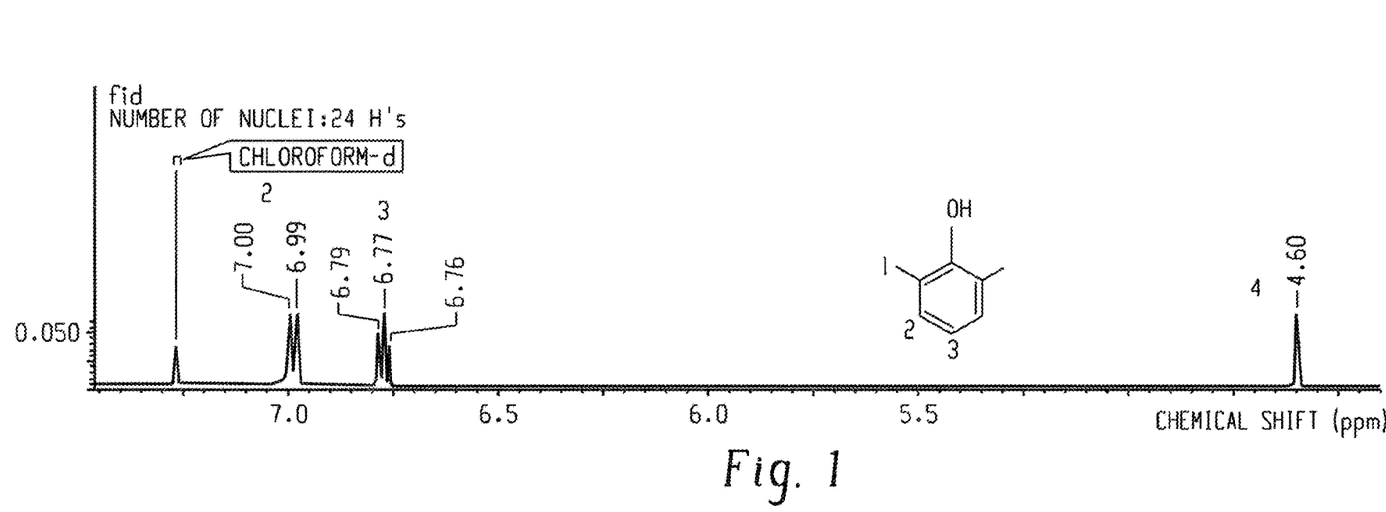
FIG. 1 is a partial (downfield) proton nuclear magnetic resonance ($^1$H NMR) spectrum for the comonomer 2,6-xylenol.

FIG. 1 is a partial (downfield) proton nuclear magnetic resonance ($^1$H NMR) spectrum for the comonomer 2,6-xylenol in deuterated chloroform.

Figure 2:
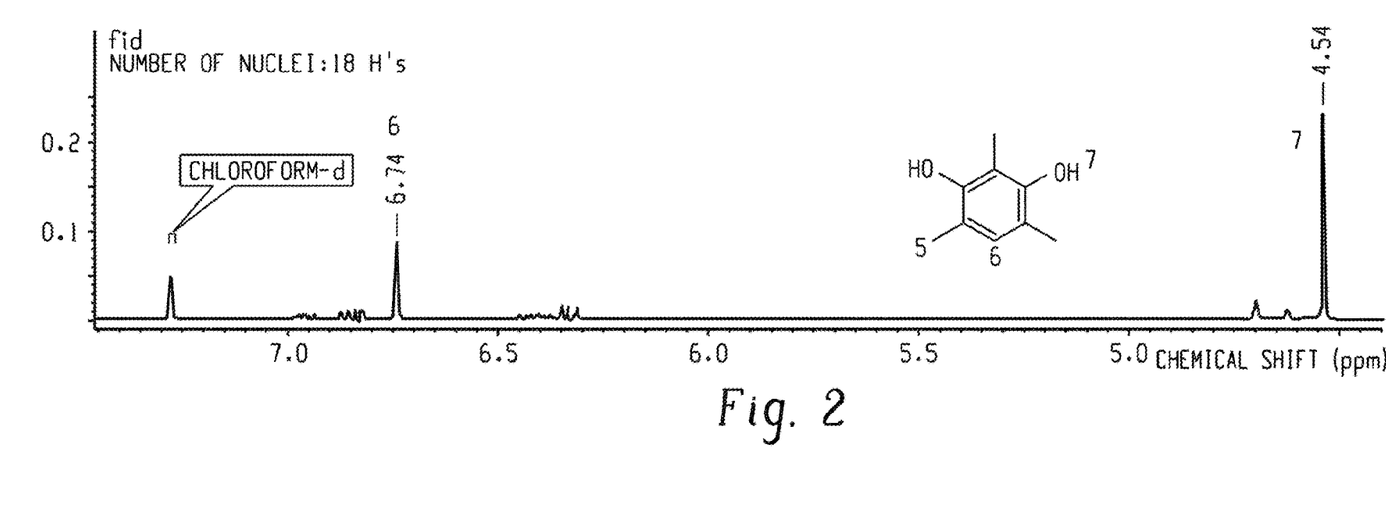
FIG. 2 is a partial (downfield) $^1$H NMR spectrum for the comonomer 2,4,6-trimethylresorcinol.

FIG. 2 is a partial (downfield)¹H NMR spectrum for the comonomer 2,4,6-trimethylresorcinol in deuterated chloroform.

Figure 3:
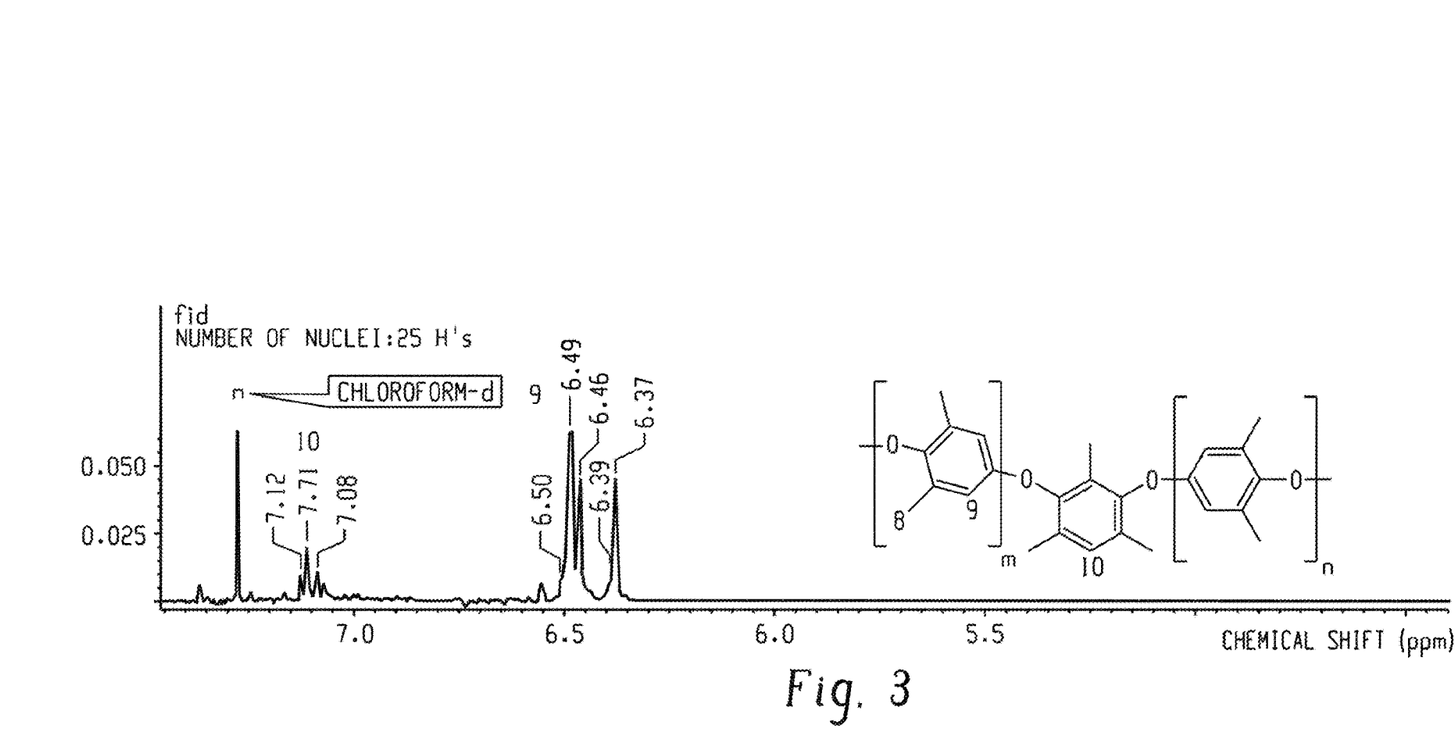
FIG. 3 is a partial (downfield) $^1$H NMR spectrum for a copolymer of 2,6-xylenol and 2,4,6-trimethylresorcinol.

FIG. 3 is a partial (downfield)¹H NMR spectrum for a copolymer of 2,6-xylenol and 2,4,6-trimethylresorcinol in deuterated chloroform. The spectrum, when compared to spectra for the respective monomers, shows the absence of peaks for the hydroxyl protons of TMR (4.56 ppm) and the absence of the 5-position proton of TMR (6.74 ppm), thereby indicating efficient incorporation of TMR into the copolymer. To provide a more sensitive measure of TMR incorporation, 5 grams of oligomer were refluxed in 25 milliliters of methanol for 30 min. The solution was filtered to remove the undissolved solids and filtrate was subjected to rotary evaporation to remove the methanol, leaving about 200 milligrams of total solids. The isolated solids were analyzed by GC for unreacted TMR. The results indicated that the oligomer contained less than 0.1 weight percent of residual TMR, based on the weight of oligomer. In a corresponding co-oligomerization of 2,6-xylenol and 2,2-bis(3,5-dimethyl-4-hydroxyphenyl)propane (TMBPA), the oligomer contained about 0.8 weight percent of residual TMBPA.

Figure 4:
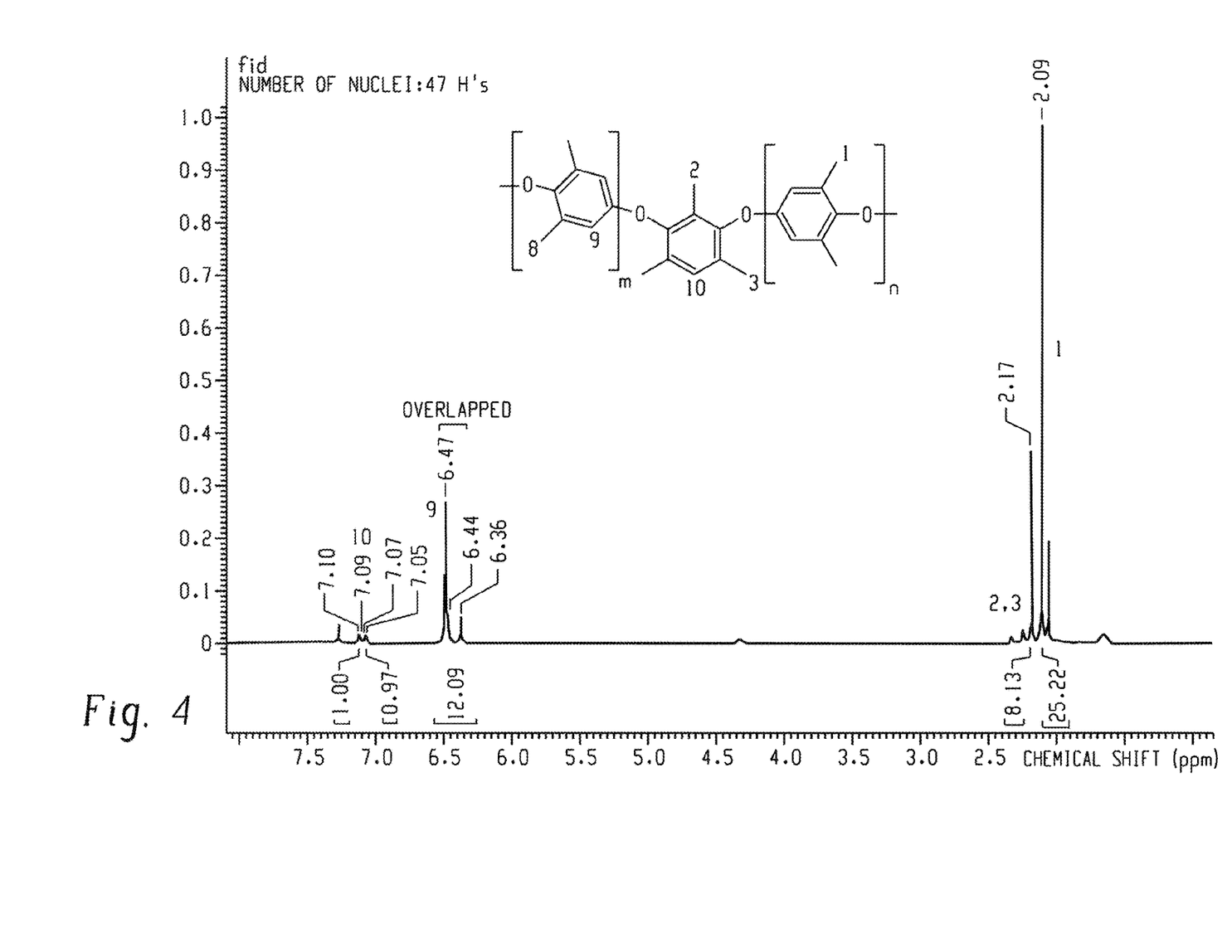
FIG. 4 is a $^1$H NMR spectrum for a copolymer of 2,6-xylenol and 2,4,6-trimethylresorcinol, with overlaid enlargements of downfield (upper left) and upfield (upper right) portions of the spectrum.

FIG. 4 is a ¹H NMR spectrum for a copolymer of 2,6-xylenol and 2,4,6-trimethylresorcinol, with overlaid enlargements of downfield (upper left) and upfield (upper right) portions of the spectrum. The spectrum indicates the presence of the TMR aromatic proton in the oligomer, and multiple peaks from 7.05 to 7.10 ppm indicate the TMR incorporation at different places of the oligomer chain. And in the aliphatic region, the three major peaks around 2.2-2.1 ppm indicate different environments of methyl groups.

Figure 5:
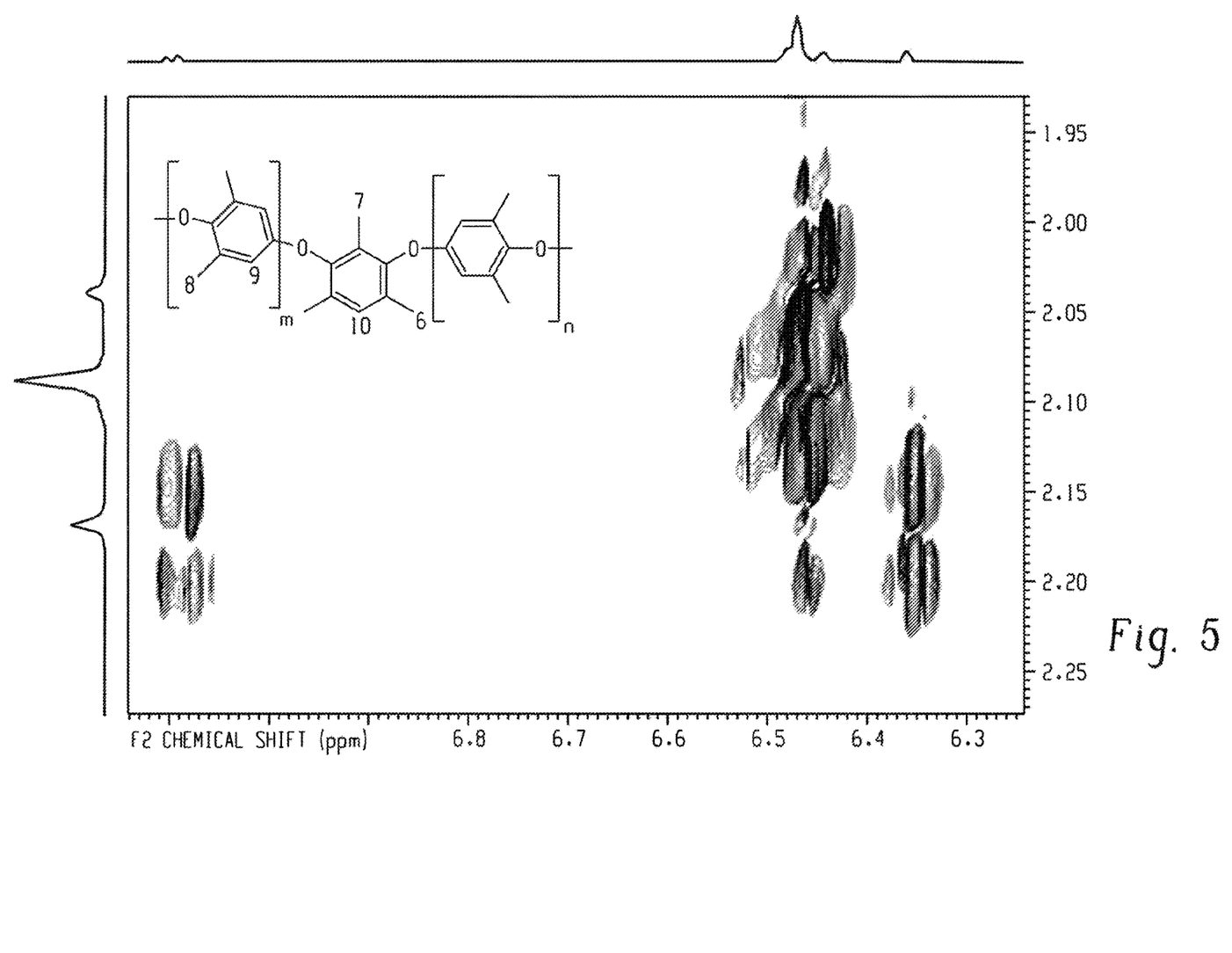
FIG. 5 is a $^1$H-$^1$H homonuclear correlation spectroscopy (COSY) two-dimensional (2D) NMR spectrum of a copolymer of 2,6-xylenol and 2,4,6-trimethylresorcinol.

FIG. 5 is a ¹H-¹H homonuclear correlation spectroscopy (COSY) two-dimensional (2D) NMR spectrum of a copolymer of 2,6-xylenol and 2,4,6-trimethylresorcinol. Two dimensional proton-proton correlations for TMR aromatic proton at carbon 10 with methyl protons at carbons 6 and 7 clearly indicate the presence of TMR in to the oligomer matrix (lower left portion of 2D spectrum). The correlation of aromatic protons from carbon 9 with their respective methyl group protons at carbon 8 indicates the presence of xylenol at different positions of the chain (right portion of the 2D spectrum).

Figure 6:
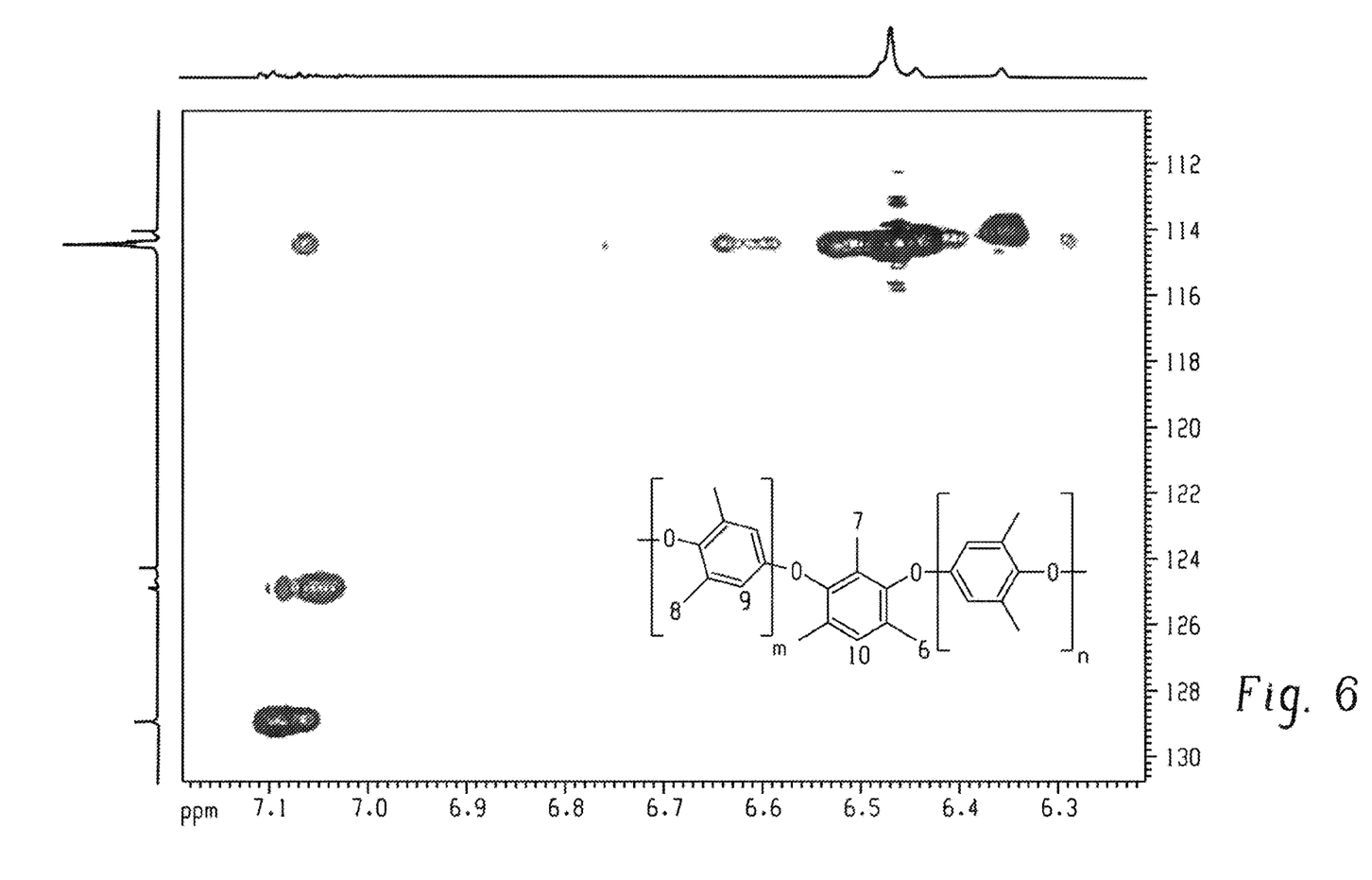
FIG. 6 shows one region of a $^1$H-$^{13}$C heteronuclear single quantum coherence (HSQC) 2D NMR spectrum of a copolymer of 2,6-xylenol and 2,4,6-trimethylresorcinol.

FIG. 6 shows one region of a ¹H-¹³C heteronuclear single quantum coherence (HSQC) 2D NMR spectrum of a copolymer of 2,6-xylenol and 2,4,6-trimethylresorcinol. The aromatic region of the spectrum shows the correlation of carbon number 10 with its proton clearly indicate the presence of TMR at two different positions in the polymer chain, possibly internal to the chain in some molecules, and at the end of the chain in other molecules.

Figure 7:
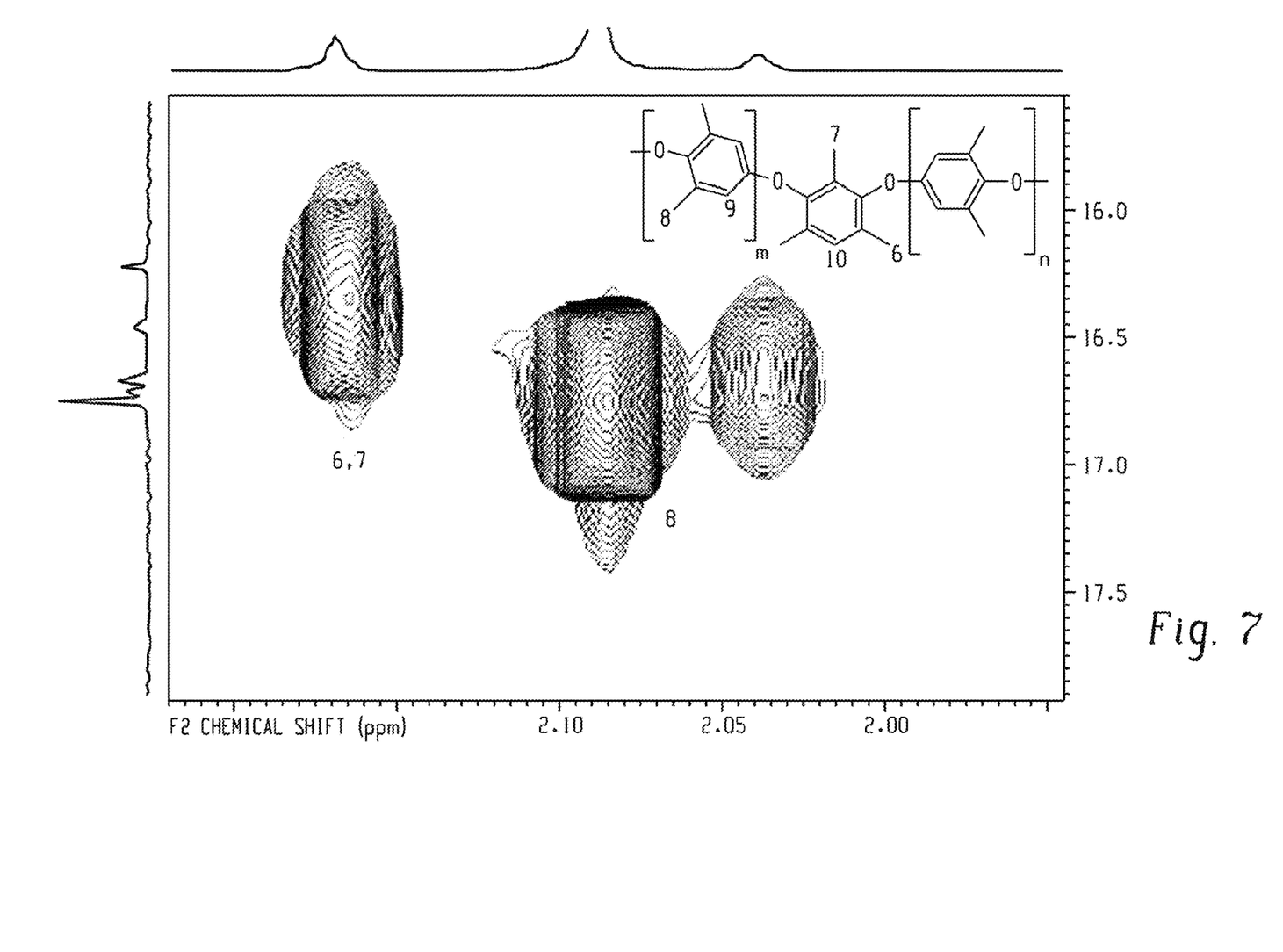
FIG. 7 shows another region of a $^1$H-$^{13}$C HSQC 2D NMR spectrum of a copolymer of 2,6-xylenol and 2,4,6-trimethylresorcinol.

FIG. 7 shows another region of a ¹H-¹³C HSQC 2D NMR spectrum of a copolymer of 2,6-xylenol and 2,4,6-trimethylresorcinol. The observation of methyl protons in different environments shows the presence of TMR in both internal and terminal positions of the oligomer chain.

The invention claimed is:

1. A copolymer having the structure wherein each occurrence of $Q^1$ and $Q^2$ is independently selected from the group consisting of halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, and $C_2$-$C_{12}$ halohydrocarbyloxy wherein at least two carbon atoms separate the halogen and oxygen atoms; each occurrence of $Q^3$ and $Q^4$ is independently selected from the group consisting of hydrogen, halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, and $C_2$-$C_{12}$ halohydrocarbyloxy wherein at least two carbon atoms separate the halogen and oxygen atoms; and m and n are independently 0 to 50, provided that, the sum of m and n is at least 3.

2. The copolymer of claim 1, wherein the sum of m and n is 3 to 15.

3. The polymer of claim 1, wherein each occurrence of $Q^1$ and $Q^2$ is independently methyl, N,N-diethylaminomethyl, N-ethylaminomethyl, or phenyl; each occurrence of $Q^3$ is hydrogen; and each occurrence of $Q^4$ is hydrogen, methyl, or phenyl.

4. The copolymer of claim 1, wherein each occurrence of $Q^1$ and $Q^2$ is independently methyl or N,N-diethylaminomethyl or N-ethylaminomethyl; and each occurrence of $Q^3$ and $Q^4$ is hydrogen.

5. The copolymer of claim 1, wherein m and n are each greater than zero.

6. The copolymer of claim 1, wherein
the sum of m and n is 3 to 15;
each occurrence of $Q^1$ and $Q^2$ is methyl or N,N-diethylaminomethyl or N-ethylaminomethyl; and
each occurrence of $Q^3$ and $Q^4$ is hydrogen.

7. A composition comprising:
the copolymer of claim 1; and
a solvent selected from the group consisting of $C_3$-$C_8$ ketones, $C_3$-$C_8$ N,N-dialkylamides, $C_4$-$C_{16}$ dialkyl ethers, $C_6$-$C_{12}$ aromatic hydrocarbons, $C_1$-$C_3$ chlorinated hydrocarbons, $C_3$-$C_6$ alkyl alkanoates, $C_2$-$C_6$ alkyl cyanides, $C_2$-$C_6$ dialkyl sulfoxides, and mixtures thereof.

8. The composition of claim 7 comprising, based on the total weight of the composition,
10 to 50 weight percent of the copolymer; and
50 to 90 weight percent of the solvent.

9. The composition of claim 7 comprising, based on the total weight of the composition,
10 to 50 weight percent of the copolymer; and
50 to 90 weight percent of the solvent, wherein the solvent is selected from the group consisting of N-methyl-2-pyrrolidone, methyl ethyl ketone, and combinations thereof.

10. A composition comprising:
the copolymer of claim 1; and
a thermosetting resin.

11. The composition of claim 10, wherein the thermosetting resin is selected from the group consisting of epoxy resins, unsaturated polyester resins, polyimide resins, bismaleimide resins, bismaleimide triazine resins, cyanate ester resins, vinyl resins, benzoxazine resins, benzocyclobutene resins, acrylics, alkyds, phenol-formaldehyde resins, novolac resins, resole resins, melamine-formaldehyde resins, urea-formaldehyde resins, unsaturated polyesterimides, and combinations thereof.

12. The composition of claim 10, wherein the thermosetting resin comprises an epoxy resin.

13. The composition of claim 10 comprising, based on the total weight of the composition,
   5 to 80 weight percent of claim 1; and
   20 to 95 weight percent of the thermosetting resin.

14. The composition of claim 10 comprising, based on the total weight of the composition,
   20 to 80 weight percent of the copolymer of claim 1, wherein the sum of m and n is 3 to 15; each occurrence of $Q^1$ and $Q^2$ is methyl or N,N-diethylaminomethyl or M-ethylaminomethyl; and each occurrence of $Q^3$ and $Q^4$ is hydrogen; and
   20 to 80 weight percent of an epoxy resin.

\* \* \* \* \*